United States Patent [19]

Maffrand

[11] 4,075,340
[45] Feb. 21, 1978

[54] THIENO [2,3-c]PYRIDINE DERIVATIVES AND THERAPEUTIC COMPOSITION CONTAINING SAME

[75] Inventor: Jean-Pierre Maffrand, Toulouse, France

[73] Assignee: Parcor, Paris, France

[21] Appl. No.: 692,186

[22] Filed: June 2, 1976

[30] Foreign Application Priority Data

June 27, 1975  France ................................ 75 20241

[51] Int. Cl.² .................... A61K 31/54; C07D 417/04
[52] U.S. Cl. .............................. 424/256; 260/294.8 C
[58] Field of Search .................. 260/294.8 C; 424/256

[56] References Cited

PUBLICATIONS

Karrer, Organic Chemistry, 4th Eng. Edition, Elsevier Pub. Co., (N.Y.), p. 928, 1950.
Chemical & Engineering News, vol. 50 p. 18, Apr. 3, 1972.
Burger, Medicinal Chemistry, Sec. Edition, p. 497, 1960.
Elderfield, Heterocyclic Compounds, vol. I, Wiley Pub., p. 485, (1950).
Klingsberg, Pyridine and its Derivatives, Part Two, Interscience Pub., pp. 50-51, (1961).
Descamps et al., Chem. Abstracts, vol. 59, (2), pp. 1605-1607, July 22, 1963.

*Primary Examiner*—Alan L. Rotman
*Attorney, Agent, or Firm*—Young & Thompson

[57] ABSTRACT

This invention relates to derivatives having the formula:

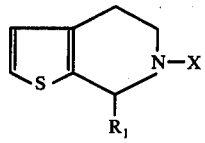

(I)

or

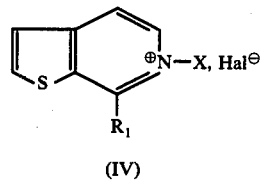

(IV)

in which $R_1$ is hydrogen or alkyl having 1-6 carbon atoms; X is $(CHR_2)_m$ in which $m$ is an integer from 2 to 15, or $(CHR_2)_n R_3$ in which $n$ is an integer from 1 to 15, $R_2$ is hydrogen, or a hydroxy, acyloxy or alkyl group having 1-6 carbon atoms, and the various symbols $R_2$ may have different meanings in each radical $(CHR_2)$ when several radicals $(CHR_2)$ are present, $R_3$ is a trichloromethyl, acetyl, carboxy or alkoxycarbonyl group, or a phenyl, phenoxy, benzoyl, thienyl or pyridyl radical optionally substituted with at least a halogen atom, or a hydroxy, nitro, amino, cyano, carboxy, alkyloxycarbonyl, alkyl having 1-6 carbon atoms, alkoxy having 1-6 carbon atoms or methylenedioxy group, and to the acid addition salts of the derivatives of the formula (I).

Said derivatives have useful anti-inflammatory and antiarrhythmic activities and an inhibiting action on blood platelet aggregation.

5 Claims, No Drawings

THIENO [2,3-c] PYRIDINE DERIVATIVES AND THERAPEUTIC COMPOSITION CONTAINING SAME

This invention relates to new thieno[2,3-c]pyridine derivatives and to their applications in human and veterinary medicine.

The new compounds of this invention have the following formula:

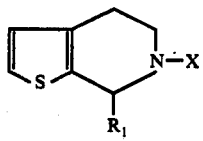

(I)

in which $R_1$ represents hydrogen or an alkyl radical having 1-6 carbon atoms; X represents $(CHR_2)_m H$ in which m is an integer from 2 to 15, or $(CHR_2)_n R_3$ in which n is an integer from 1 to 15, $R_2$ represents hydrogen, or a hydroxy, acyloxy or alkyl group having 1-6 carbon atoms, and the various symbols $R_2$ may have different meanings in each radical $(CHR_2)$ when several radicals $(CHR_2)$ are present, $R_3$ represents a trichloromethyl, acetyl, carboxy or alkoxycarbonyl group, or a phenyl, phenoxy, benzoyl, thienyl or pyridyl radical optionally substituted with at least a halogen atom, or a hydroxy group, a nitro group, and amino group, a cyano group, a carboxy group, an alkyloxycarbonyl group, an alkyl group having 1-6 carbon atoms, an alkoxy group having 1-6 carbon atoms or a methylenedioxy group.

The invention includes also within its scope the acid addition salts with inorganic or organic acids of the derivatives of the formula (I).

A process for the preparation of compounds of the formula (I) comprises condensing a compound of the formula:

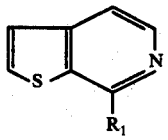

(II)

in which $R_1$ has the above-defined meaning, with a halide having the formula:

Hal—X  (III)

in which Hal represents a halogen atom and X has the above-defined meaning, to give a pyridinium salt having the formula:

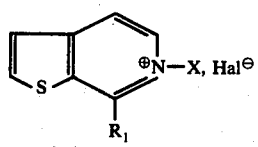

(IV)

and subsequently hydrogenating the resulting pyridinium salt, to give the desired derivative of the formula (I).

The pyridinium salts of the formula (IV) are new compounds and also possess useful therapeutic activities. They constitute a further feature of this invention.

The compounds of the formula (I) may also be prepared by treatment of a 4,5,6,7-tetrahydro-thieno[2,3-c]pyridine with a halide of the formula (III), according to the following reaction scheme:

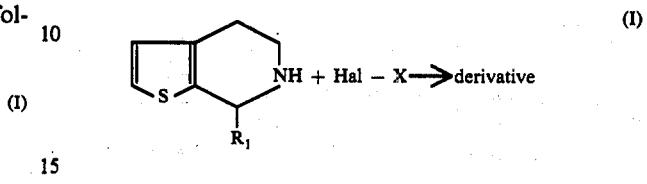

The resulting derivatives of the formula (I) may be isolated as such or in salt form.

The condensation reaction is preferably conducted within a medium consisting of an inert solvent such as acetonitrile, for example.

A reducing derivative such as an alkali metal borohydride, sodium borohydride, for example, is advantageously used as hydrogenating agent. Said reduction is normally effected at room temperature.

According to a modification, the compounds of the formula (I) in which $R_2$ is an acyloxy group may be prepared from the corresponding compounds in which $R_2$ is a hydroxy group, by reaction with an acid anhydride, such as acetic anhydride, for example.

The starting thieno[2,3-c]pyridines of the formula (II) are known compounds which have been described in the literature.

The purification of the compounds obtained according to the above process is preferably effected by extraction with an organic solvent such as ether, after addition of a base (e.g., ammonia), evaporating off the solvent and taking up the residue into an acid (HCl, for example) which causes precipitation as crystals which may be recrystallized, after filtration, from ethanol.

The salts and the quaternary ammonium derivatives of the compounds of the formula (I) may be prepared by methods well known by those expert in the art.

The following non limiting Examples are given to illustrate the preparation of compounds of this invention.

EXAMPLE 1

Preparation of 6-n-dodecyl-4,5,6,7-tetrahydro-thieno[2,3-c]pyridine (Derivative No. 1)

(a) A mixture of thieno[2,3-c]pyridine (7 g; 0.052 mole), 1-bromododecane (13 g; 0.052 mole) and acetonitrile (100 cc) is refluxed during 4 hours. The solution is then concentrated in vacuo and the residue is triturated with ether to give, after filtration and drying, 12 g (Yield: 60%; m.p. = 95-100° C) 6-dodecyl-thieno[2,3-c]pyridinium bromide (derivative of the formula (IV)).

(b) The salt obtained in (a) (11.5 g; 0.030 mole) is dissolved in water (50 cc) and ethanol (200 cc) and sodium borohydride (2.3 g) is added portionwise thereto. After stirring overnight at room temperature, excess borohydride is destroyed by addition of acetone. The mixture is concentrated in vacuo and the residual oil is dissolved in methylene chloride. The resulting solution is washed with water, dried over sodium sulfate and concentrated in vacuo. The oily residue (9.6 g) is converted to the maleate which is recrystallized from isopropyl ether-isopropanol (M.p. = 146° C. Reduction yield: 80.5%).

EXAMPLE 2

Preparation of 6-dodecyl-7-methyl-4,5,6,7-tetrahydro-thieno[2,3-c]pyridinium iodide (Derivative No. 2)

A mixture of 6-dodecyl-4,5,6,7-tetrahydro-thieno[2,3-c]pyridine (2.4g; 7.17 mmoles), methyl iodide (0.9 cc) and acetonitrile (30 cc) is refluxed during 2 hours. The reaction mixture is concentrated in vacuo and the residue is crystallized from ether. The resulting crystals are filtered off, washed with ether, dried in vacuo and recrystallized from ethanol (M.p. = 120° C; Yield: 95%).

EXAMPLE 3

Preparation of 7-methyl-6-(3,4,5-trimethoxy-benzyl)-4,5,6,7-tetrahydro-thieno[2,3-c]pyridine (Derivative No. 3)

(a) A mixture of 7-methyl-thieno[2,3-c]pyridine (3.90 g; 26.2 mmoles), 3,4,5-trimethoxy-benzyl chloride (5.67 g; 26.2 mmoles) and acetonitrile (40 cc) is refluxed during 5 hours. The mixture is then concentrated in vacuo and the residue is crystallized from acetone. The resulting crystals are filtered off, washed with ether and dried in vacuo (M.p. = 203°-204° C; Yield: 37%).

(b) The product obtained in (a) (3.5 g; 9.58 mmoles) is dissolved in water (24 cc) and ethanol (72 cc), and sodium borohydride (3 g) is added portionwise thereto. After stirring overnight at room temperature, the reaction medium is made acidic with 2N hydrochloric acid, made basic with 2N sodium hydroxide and extracted with methylene chloride. The organic extracts are washed with water, dried over sodium sulfate and concentrated in vacuo. The residue is converted to the hydrochloride which is recrystallized from ethyl acetate-ethanol (M.p. = 180°-186° C. Reduction yield: 54%).

EXAMPLE 4

Preparation of 6-o-methoxycarbonylbenzyl-4,5,6,7-tetrahydro-thieno[2,3-c]pyridine (Derivative No. 4)

(a) A mixture of thieno[2,3-c]pyridine (15 g; 0.111 mole), methyl 2-bromomethylbenzoate (26.7 g; 0.116 mole) and acetonitrile (150 cc) is refluxed during 2 hours. After cooling, the resulting crystals are filtered off, washed with ether and dried in vacuo (M.p. = 170° C. Yield: 93%).

(b) The compound obtained in (a) above (37.6 g; 0.103 mole) is dissolved in water (100 cc) and ethanol (400 cc), after which sodium borohydride (7.85 g) is added thereto portionwise, while cooling in an ice-bath. After stirring overnight at room temperature, the excess borohydride is destroyed by addition of acetone, the resulting material is concentrated in vacuo and extracted with ether. The organic extracts are washed with water, dried over sodium sulfate and concentrated in vacuo. The residual oil is then converted to the maleate (M.p. = 144° C. Reduction yield = 73.5%).

EXAMPLE 5

Preparation of 6-o-carboxybenzyl-4,5,6,7-tetrahydro-thieno[2,3-c]pyridine (Derivative No. 5)

A mixture of 6-o-methoxycarbonylbenzyl-4,5,6,7-tetrahydro-thieno[2,3-c]pyridine (19 g; 0.066 mole), soda lye ($d$ = 1.38; 20 cc) and ethanol (200 cc) is refluxed during one hour. The solution is exactly neutralized with 6N hydrochloric acid, concentrated in vacuo, and the residue is extracted with methylene chloride. The organic extracts are dried over sodium sulfate and concentrated in vacuo. The resulting crystals are recrystallized from benzene (M.p. = 151° C. Yield: 52%).

EXAMPLE 6

Preparation of 6-[2-(5-chloro-thienyl)-methyl]-4,5,6,7-tetrahydro-thieno[2,3-c]pyridine (Derivative No. 6)

(a) A mixture of thieno[2,3-c]pyridine (10 g; 0.074 mole), and 5-chloro-2-chloromethyl-thiophene (13.95 g; 0.083 mole) in acetonitrile (80 cc) is refluxed during 4 hours. After cooling, the resulting crystals are filtered off, washed with ether and dried in vacuo (M.p. = 158° C. Yield = 88.5%).

(b) The salt obtained above in (a) (19.8 g; 0.066 mole) is dissolved in water (100 cc) and ethanol (400 cc), after which sodium borohydride (5 g) is added portionwise thereto, with cooling. After stirring overnight at room temperature, the solution is concentrated in vacuo, made acidic with 3N hydrochloric acid, then made basic with concentrated ammonia and extracted with methylene chloride. The organic extracts are washed with water, dried over sodium sulfate and concentrated in vacuo. The residual oil (16.3 g) is converted to the hydrochloride which is then recrystallized from 95% ethanol (M.p. = 200° C. Yield = 35%).

EXAMPLE 7

Preparation of 6-(2-hydroxy-2-phenyl-ethyl)-7-methyl-4,5,6,7-tetrahydro-thieno[2,3-c]pyridine (Derivative No. 7)

(a) A mixture of 7-methyl-thieno[2,3-c]pyridine (6 g; 40.2 mmoles), phenacyl bromide (8.08 g; 40.6 mmoles) and acetone (30 cc) is stirred at room temperature during 6 hours. The solvent is then evaporated off in vacuo, after which the 7-methyl-6-phenacyl-thieno[2,3-c]pyridinium bromide is precipitated from diethyl ether, filtered, washed with ether and dried in vacuo (M.p. = 255°-260° C. Yield = 71%).

(b) The above product (10 g; 29 mmoles) is dissolved in water (35 cc) and ethanol (140 cc), after which sodium borohydride (2.2 g) is added portionwise thereto. After stirring overnight at room temperature, the excess borohydride is destroyed by addition of acetone. The solution is concentrated in vacuo and extracted with methylene chloride. The organic extracts are washed with water, dried over sodium sulfate and concentrated in vacuo. The oily residue is converted to the hydrochloride which is recrystallized from acetonitrile (M.p. = 212° C. Yield = 41%).

EXAMPLE 8

Preparation of 6-(2-acetoxy-2-p-chlorophenyl-ethyl)-4,5,6,7-tetrahydro-thieno[2,3-c]pyridine (Derivative No. 8)

A solution of 6-(2-p-chlorophenyl-2-hydroxy-ethyl)-4,5,6,7-tetrahydro-thieno[2,3-c]pyridine (6 g; 20.4 mmoles) in acetic anhydride (12 cc) and pyridine (30 cc) is stirred at room temperature during 4 hours. After concentrating the mixture in vacuo, the residue is poured over ice, made basic with ammonia and extracted with ether. The organic extracts are washed with water, dried over sodium sulfate and concentrated in vacuo. The resulting crystals are recrystallized from isopropanol (M.p. = 92° C. Yield = 80%).

Using analogous procedures, the following derivatives were prepared:

derivative No. 9 : 6-(2-hydroxy-propyl)-4,5,6,7-tetrahydro-thieno[2,3-c]pyridine, hydrochloride; white crystals, m.p. = 212° C.

derivative No. 10 : 6-(2-acetoxy-2m.methoxyphenylethyl)-4,5,6,7-tetrahydro-thieno[2,3-c]pyridine; white crystals; m.p. = 80° C.

derivative No. 11 : 6-o-nitrobenzyl-4,5,6,7-tetrahydrothieno[2,3-c]pyridine, hydrochloride; white crystals; m.p. = 100° C (decomposition).

derivative No. 12 : 6-p-nitrobenzyl-4,5,6,7-tetrahydrothieno[2,3-c]pyridine; brown crystals; m.p. = 116°–118° C derivative No. 13 : 6-o-cyanobenzyl-4,5,6,7-tetrahydrothieno[2,3-c]pyridine, maleate; pale green crystals; m.p. = 168° C.

derivative No. 14 : 6-(2-p.chlorophenyl-2-hydroxyethyl)-7-methyl-4,5,6,7-tetrahydro-thieno[2,3-c]pyridine, hydrochloride; white crystals; m.p. = 201°–203° C.

derivative No. 15 : 6-o-chlorobenzyl-7-methyl-4,5,6,7-tetrahydro-thieno[2,3-c]pyridine, oxalate; off-white crystals; m.p. = 142° C.

derivative No. 16 : 6-(2-chloro-benzyl)-4,5,6,7-tetrahydro-thieno[2,3-c]pyridine, maleate; white crystals; m.p. = 187° C.

derivative No. 17 : 6-(3,4,5-trimethoxy-benzyl)-4,5,6,7-tetrahydro-thieno[2,3-c]pyridine, maleate; white crystals; m.p. = 168° C.

derivative No. 18 : 6-p.methoxybenzyl-4,5,6,7-tetrahydro-thieno[2,3-c]pyridine, hydrochloride; yellowish-white material; m.p. = 198°–200° C.

derivative No. 19 : 6-β-phenethyl-4,5,6,7-tetrahydro-thieno[2,3-c]pyridine, hydrochloride; white crystals; m.p. 238° C.

derivative No. 20 : 6-m.methoxybenzyl-4,5,6,7-tetrahydro-thieno-[2,3-c]pyridine, hydrochloride; white crystals; m.p. = 208° C.

derivative No. 21 : 6-p.chlorobenzyl-4,5,6,7-tetrahydro-thieno[2,3-c]pyridine, hydrochloride; white crystals; m.p. = 235° C (decomposition)

derivative No. 22 : 6-m.chlorobenzyl-4,5,6,7-tetrahydro-thieno-[2,3-c]pyridine, hydrochloride; yellowish-white crystals; m.p. > 240° C.

derivative No. 23 : 6-(2-hydroxy-2-phenyl-ethyl)-4,5,6,7-tetrahydro-thieno[2,3-c]pyridine, hydrochloride; white crystals; m.p. = 210°–212° C.

derivative No. 24 : 6-p.methylbenzyl-4,5,6,7-tetrahydro-thieno[2,3-c]pyridine, hydrochloride; white crystals; m.p. = 240° C (decomposition).

derivative No. 25 : 6-(3,4-dimethoxy-benzyl)-4,5,6,7-tetrahydro-thieno[2,3-c]pyridine, hydrochloride, white crystals; m.p. = 216° C.

derivative No. 26 : 6-o.fluorobenzyl-4,5,6,7-tetrahydro-thieno[2,3-c]pyridine, fumarate; white crystals; m.p. = 173° C.

derivative No. 27 : 6-(2-hydroxy-2-p.chlorophenyl-ethyl)-4,5,6,7-tetrahydro-thieno[2,3-c]pyridine; white crystals; m.p. = 122° C.

derivative No. 28 : 6-(2,3,4-trimethoxy-benzyl)-4,5,6,7-tetrahydro-thieno[2,3-c]pyridine, oxalate; white crystals; m.p. = 175° C.

derivative No. 29 : 6-(2-hydroxy-2-p.fluorophenylethyl)-4,5,6,7-tetrahydro-thieno[2,3-c]pyridine; white crystals, m.p. = 102° C.

derivative No. 30 : 6-(2-hydroxy-2-p.methoxyphenylethyl)-4,5,6,7-tetrahydro-thieno[2,3-c]pyridine; white crystals; m.p. = 106° C.

derivative No. 31 : 7-methyl-6-β-phenethyl-4,5,6,7-tetrahydro-thieno[2,3-c]pyridine, maleate; white crystals; m.p. = 162° C.

derivative No. 32 : 6-(2-hydroxy-2-p.methoxyphenylethyl)-7-methyl-4,5,6,7-tetrahydro-thieno[2,3-c]pyridine; off-white crystals; m.p. = 169°–171° C.

derivative No. 33 : 6-(2-hydroxy-2-m.methoxyphenylethyl)-7-methyl-4,5,6,7,-tetrahydro-thieno[2,3-c]pyridine; creamy-white crystals; m.p. = 143°–145° C.

derivative No. 34 : 6-[2-(2,5-dimethoxy-phenyl)-2-hydroxy-ethyl]-7-methyl-4,5,6,7-tetrahydro-thieno[2,3-c]pyridine; white crystals; m.p. = 207°–209° C.

derivative No. 35 : 6-(2-hydroxy-3-p.methoxyphenoxypropyl)-4,5,6,7-tetrahydro-thieno[2,3-c]pyridine, hydrochloride; white crystals; m.p. = 152° C.

derivative No. 36 : 6-(3-oxo-butyl)-4,5,6,7-tetrahydrothieno[2,3-c]-pyridine, maleate; white crystals; m.p. = 131° C.

derivative No. 37 : 6-(2-hydroxy-3,3,3-trichloropropyl)-4,5,6,7-tetrahydro-thieno[2,3-c]pyridine; white crystals; m.p. = 150° C.

derivative No. 38 : 6-(3,4-dimethoxy-benzyl)-4,5,6,7-tetrahydro-thieno[2,3-c]pyridine; white crystals; m.p. = 216° C.

The following derivatives of the formula (IV) were also prepared:

derivative No. 39 : 7-methyl-6-phenacyl-thieno[2,3-c]pyridinium bromide; m.p. = 255°–260° C. Intermediate compound, the preparation of which is described in step (a) of Example 7.

derivative No. 40 : 6-phenacyl-thieno[2,3-c]pyridinium bromide; white crystals; m.p. = 248° C; intermediate of derivative No. 23 derivative No. 41 : 6-p-chlorophenacyl-thieno[2,3-c]pyridinium bromide, semi-hydrate; white crystals; m.p. = 243° C; intermediate of derivative No. 27.

derivative No. 42 : 6-p-fluorophenacyl-thieno[2,3-c]pyridinium bromide, semi-hydrate; pale cream crystals; m.p. = 210° C; intermediate of derivative No. 29.

derivative No. 43 : 6-p-methoxyphenacyl-thieno[2,3-c]pyridinium bromide; white crystals; m.p. > 260° C; intermediate of derivative No. 30.

derivative No. 44 : 7-methyl-6-p-methoxyphenacyl-thieno[2,3-c]pyridinium bromide; white crystals; m.p. > 260° C; intermediate of derivative No. 32.

derivative No. 45 : 6-o-methoxyphenacyl-7-methyl-thieno[2,3c-]pyridinium bromide; white crystals; m.p. = 243° C.

derivative No. 46 : 6-(2,4-dichloro-phenacyl)-7-methyl-thieno[2,3-c]pyridinium iodide; yellow crystals; m.p. = 194° C.

derivative No. 47 : 6-p-chlorophenacyl-7-methyl-thieno[2,3-c]pyridinium bromide; white crystals; m.p. > 260° C.

derivative No. 48 : 6-(2-picolyl-N-oxide)-thieno[2,3-c]pyridinium chloride; white crystals; m.p. 230° C (decomp.).

derivative No. 49 : 6-p-fluorophenacyl-7-methyl-thieno[2,3-c]pyridinium iodide; pale yellow crystals; m.p. = 220° C.

derivative No. 50 : 6-2,5-dimethoxy)-7-methyl-thieno[2,3-c]pyridinium bromide; white crystals; m.p. 252° C. Intermediate of derivative No. 34.

derivative No. 51 : 6-m-methoxyphenacyl-7-methyl-thieno[2,3-c]pyridinium bromide; white crystals; m.p. = 245° C; intermediate of derivative No. 33.

derivative No. 52 : 6-(3,4-dihydroxy-phenacyl)-7-methyl-thieno[2,3-c]pyridinium iodide; brown crystals; m.p. > 260° C.

derivative No. 53 : 7-methyl-6-p-methylphenacyl-thieno[2,3-c]pyridinium bromide; white crystals; m.p. > 260° C.

derivative No. 54 : 6-p-hydroxyphenacyl-7-methyl-thieno[2,3-c]pyridinium bromide; brown crystals; m.p. > 260° C.

derivative No. 55 : 6-ethoxycarbonylmethyl-thieno[2,3-c]pyridinium bromide; white crystals; m.p. > 260° C.

derivative No. 56 : 6-acetonyl-thieno[2,3-c]pyridinium chloride; white crystals; m.p. > 260° C.

derivative No. 57 : 6-(2-carboxy-ethyl)-thieno[2,3-c]pyridinium chloride; white crystals; m.p. = 246°-248° C.

derivative No. 58 : 6-carboxymethyl-thieno[2,3-c]-pyridinium chloride; pale pink crystals; m.p. = 170° C.

The results of toxicological and pharmacological tests reported hereinafter demonstrate the good tolerance and the activities of the derivatives of this invention, particularly their anti-inflammatory, anti-arrhythmic activities and their inhibiting activity on blood platelet aggregation.

Thus, this invention relates also to a therapeutic composition having in particular anti-inflammatory, anti-arrhythmic activities and an inhibiting activity on blood platelet aggregation, comprising as active ingredient, a derivative of the formula (I) or a derivative of the formula (IV) or a pharmaceutically acceptable acid addition salt of a derivative of the formula (I), together with a pharmaceutically acceptable carrier.

I. TOXICOLOGICAL INVESTIGATION

Said investigation demonstrates the low toxicity of the derivatives of this invention.

For indicative purposes, the $LD_{50}$/24 hrs/kg body weight, determined by the intravenous route by the method according to Miller and Tainter, is 135 mg for derivative No. 6, 120 mg for derivative No. 9, 80 mg for derivative No. 10, 160 mg for derivative No. 11, 80 mg for derivative No. 17, 60 mg for derivative No. 18, 48 mg for derivative No. 19, 63 mg for derivative No. 20, 55 mg for derivative No. 21, 67 mg for derivative No. 23, 45 mg for derivative No. 24, 90 mg for derivative No. 25, 87 mg for derivative No. 26, 45 mg for derivative No. 27, 60 mg for derivative No. 29, 53 mg for derivative No. 31, 84 mg for derivative No. 34, 19 mg for derivative No. 35, 16 mg for derivative No. 36, 18 mg for derivative No. 37, 22 mg for derivative No. 38, 35 mg for derivative No. 39 and 51 mg for derivative No. 44.

Experimentation has shown that the derivatives of this invention were well tolerated throughout the acute, chronic or delayed toxicity tests and that no anomaly could be found on autopsy of the sacrificed animals.

II. PHARMACOLOGICAL INVESTIGATION

1. Anti-inflammatory Action a) Localized Carrageenin-induced Edema Method 0.1 ml of a 1% carrageenin solution is injected at time 0 in the metatarsal flexor muscles of the right hind limb of rats. The animals of the treated group are administered orally, additionally, 100 mg/kg of the test derivative, respectively one hour prior to and then simultaneously with the phlogogenic agent, and then one hour and 2.5 hours thereafter. The determinations effected with a ROCH micrometer at times 0, 1 hour, 2 hrs, 3 hrs and 5hrs after carrageenin administration, make it possible to determine the percent anti-inflammatory activity, as a function of time. The results obtained are tabulated in following Table I:

TABLE I

| Derivative n° | Percent anti-inflammatory activity | | |
|---|---|---|---|
| | after 1 hour | after 2 hours | after 5 hours |
| 1 | 38 | 46 | 54 |
| 5 | 44 | 52 | 60 |
| 8 | 40 | 49 | 59 |
| 10 | 43 | 50 | 56 |
| 14 | 40 | 46 | 52 |
| 15 | 37 | 42 | 49 |
| 23 | 39 | 51 | 58 |
| 28 | 43 | 52 | 61 |
| 30 | 38 | 44 | 51 |
| 34 | 37 | 48 | 58 | b) Ovalbumin-induced Systemic Edema Method

Rats are administered a simultaneous intraperitoneal injection of 1 ml ovalbumin and 0.5 ml of a 1% aqueous Evans Blue solution. The animals of the treated group are additionally administered orally 100 mg/kg of the test derivative, one hour prior to ovalbumin administration and then simultaneously with said ovalbumin administration. The intensity of the phenomenon thus induced is rated according to a scale from 1 to 5, according to the progress of the inflammatory syndrome. The measurements are effected after 2 hours and after 3 hours. Thus are determined the mean intensity of the edema and the percent decrease of the edema reaction. The results obtained are set forth in following Table II:

TABLE II

| Derivative n° | Percent decrease | |
|---|---|---|
| | After 2 hours | After 3 hours |
| 1 | 36 | 51 |
| 5 | 42 | 61 |
| 8 | 45 | 58 |
| 10 | 48 | 55 |
| 14 | 41 | 48 |
| 15 | 46 | 55 |
| 23 | 50 | 61 |
| 28 | 45 | 63 |
| 30 | 39 | 59 |
| 34 | 45 | 61 |

2. Anti-arrhythmic Action a) Against Adrenalin

The test is effected in chloralosed dogs administered 5 μg/kg adrenalin, by the intravenous route. Three minutes prior to said administration, the treated dogs were given 10 mg/kg of the test derivative. While severe tachyarrhythmia is found to occur in the reference dogs, the treated dogs, in contrast, are found to be efficiently protected against the arrhythmic effects induced by injection of high dosages of adrenalin.

b) Against Ouabaine

Chloralosed dogs are administered ouabaine, by the intraveneous route, at a dosage of 80 μg/kg. Highly severe arrhythmia is found to occur in the animals, 15-20 minutes after said injection. As soon as the arrhythmia sets in, the animals are administered intravenously 10 mg/kg of the test derivative. Both the sinus rhythm and the perturbed electric activity of the heart are found to be restored very rapidly by the derivatives of this invention.

c) Disorders of the cardiac rhythm appear also in dogs after ligation of the coronary artery. On injection at a dosage of 10 mg/kg, the derivatives of this invention are found capable of rapidly restoring a normal cardiac activity.

On the average, the anti-arrhythmic activity was found to be greater with the derivatives of the formula (IV) than with the derivatives of the formula (I).

3. Inhibiting Activity On Blood Platelet Aggregation

Rat plasma, prepared to contain 600,000+20,000 blood platelets per mm3 is normally cloudy. Addition of adenosine diphosphate induces blood platelet aggregation and, thus an increase of the light transmission. When the same test is effected with a plasma prepared from the blood of an animal which has been administered 100 mg/kg of a derivative having an inhibiting effect on blood platelet aggregation, there is no aggregation of the blood platelets and the serum remains cloudy. The turbidimetric assay effected with a spectrophotometer provides a measure of the inhibiting activities of the test derivatives on blood platelet aggregation.

The tests carried out with groups of five rats (three controls and two treated animals) show that the compounds of this invention induce a substantial percent inhibition on blood platelet aggregation, said percent inhibition being respectively 91% for derivative No. 3, 85% for derivative No. 7, 89% for derivative No. 9, 75% for derivative No. 12, 78% for derivative No. 18, 91% for derivative No. 21, 78% for derivative No. 24, 86% for derivative No. 27, 89% for derivative No. 29 and 74% for derivative No. 33.

The toxicological and pharmacological investigations reported above show that the derivatives of this invention are endowed with a good tolerance and possess valuable anti-inflammatory and anti-arrhythmic activities together with an inhibiting action on blood platelet aggregation.

For oral administration, the composition of this invention may be formulated as tablets, coated tablets, capsules, drops or syrups. It may also be formulated for rectal administration, as suppositories and, for parenteral administration, as injectable solutions.

Each unit dose contains advantageously from 0.010 g to 0.300 g active ingredient, the daily dosage regimen varying within a range from 0.010 g to 0.900 g active ingredient, depending on the age of the patient and the severity of the condition to be treated.

Non-limiting Examples of pharmaceutical formulations of the composition of this invention are given below.

EXAMPLE 9

| Tablets | |
|---|---|
| derivative n° 1 | 0.100 g |
| potato starch | 0.010 g |
| talc | 0.005 g |
| magnesium stearate | 0.005 g |
| stearic acid | 0.010 g |
| sugar | 0.025 g |

EXAMPLE 10

| Coated tablets | | |
|---|---|---|
| Core | derivative n° 44 | 0.050 g |
| | Levilite | 0.010 g |
| | magnesium stearate | 0.010 g |
| | starch | 0.005 g |
| Coating | gum tragacanth | 0.003 g |
| | shellac | 0.002 g |
| | gum arabic | 0.002 g |
| | glucose | 0.010 g |
| | talc | 0.001 g |
| | Blue | traces |
| | sugar, sufficient for 1 coated tablet | |

EXAMPLE 11

| CAPSULES | |
|---|---|
| derivative n° 24 | 0.150 g |
| lactose | 0.005 g |
| magnesium stearate | 0.005 g |
| starch | 0.005 g |
| colloidal silica | 0.010 g |

EXAMPLE 12

| SYRUP | |
|---|---|
| derivative n° 27 | 2.50 g |
| sweetened flavoured excipient, sufficient to make | 100 ml |

EXAMPLE 13

| INJECTABLE SOLUTION | | |
|---|---|---|
| derivative n° 36 | 0.125 g | |
| isotonic solution, sufficient to make | 2 | ml |

In view of its anti-inflammatory and antiarrhythmic properties and of its inhibiting effect on blood platelet aggregation, the composition of this invention is usefully applicable in the treatment of the various stages of inflammation. It is applicable in chronic inflammatory rheumatism, degenerative rheumatism, in abarticular conditions, in oto-rhino-laryngology, in stomatology, in post-opertive surgery and in traumatology.

In view of its anti-arrhythmic action and of its inhibiting action on blood platelet aggregation, the composition of this invention is applicable in the treatment of disorders of the cardiac rhythm such as sinus tachycardia, fibrillation and auricular flutter, supra-ventricular tachycardia, extrasystoles and also of disorders of the cerebral and peripheral circulatory system.

Having now described my invention what I claim as new and desire to secure by Letters Patent is:

1. A compound having the following structure:

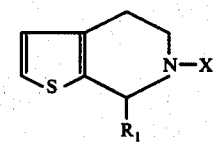

in which $R_1$ is a member selected from the group consisting of hydrogen and methyl, with a proviso that when $R_1$ is hydrogen, X is a member selected from the group consisting of
 n-dodecyl, o-methoxycarbonylbenzyl
o-carboxybenzyl
2-(5-chloro-thienyl)-methyl
2-acetoxy-2-p-chlorophenyl-ethyl
2-hydroxy-propyl
2-acetoxy-2-m.methoxyphenyl-ethyl
o-nitrobenzyl
p-nitrobenzyl
o-cyanobenzyl
2-chloro-benzyl
3,4,5-trimethoxy-benzyl
β-phenethyl
m.methoxybenzyl
p.chlorobenzyl
m.chlorobenzyl
2-hydroxy-2-phenyl-ethyl
p.methylbenzyl
3,4-dimethoxy-benzyl
o.fluorobenzyl
2-hydroxy-2- p.chlorophenyl-ethyl
2,3,4-trimethoxy-benzyl
2-hydroxy-2-p.fluorophenyl-ethyl
2-hydroxy-2-p.methoxyphenyl-ethyl
2-hydroxy-3-p.methoxyphenoxy-propyl
3-oxo-butyl
2-hydroxy-3,3,3-trichloro-propyl
3,4-dimethoxy-benzyl and when $R_1$ is methyl, X is a member selected from the group consisting of
3,4,5-trimethoxy-benzyl
2-hydroxy-2-phenyl-ethyl
2-p.chlorophenyl-2-hydroxy-ethyl
o-chlorobenzyl
2-hydroxy-2-p.methoxyphenyl-ethyl
2-hydroxy-2-m.methoxyphenyl-ethyl
2-(2,4-dimethoxy-phenyl)-2-hydroxyethyl.

2. A compound having the following structure:

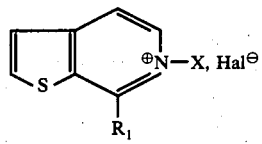

in which $R_1$ is a member selected from the group consisting of hydrogen and methyl, with a proviso that when $R_1$ is hydrogen, X is a member selected from the group consisting of
dodecyl
phenacyl
p-chlorophenacyl
p-fluorophenacyl
p-methoxyphenacyl
2-picolyl-N-oxide
ethoxycarbonylmethyl
acetonyl
2-carboxy-ethyl
carboxymethyl and when $R_1$ is methyl, X is a member selected from the group consisting of
phenacyl
p-methoxyphenacyl
o-methoxyphenacyl
2,4-dichloro-phenacyl
p-chlorophenacyl
p-fluorophenacyl
2,5-dimethoxy
m-methoxyphenacyl
3,4-dihydroxy-phenacyl
p-methylphenacyl
p-hydroxyphenacyl.

3. Therapeutic composition having an anti-inflammatory activity, comprising, as active ingredient, a compound according to claim 1 together with a pharmaceutically acceptable carrier, in unit dosage form, each unit dose containing 0.010–0.300 g active ingredient.

4. Therapeutic composition having an inhibiting activity on blood platelet aggregation, comprising, as active ingredient, a compound according to claim 1 together with a pharmaceutically acceptable carrier, in unit dosage form, each unit dose containing 0.010–0.300 g active ingredient.

5. Therapeutic composition having an anti-arrhythmic activity, comprising, as active ingredient, a compound as claimed in claim 2, together with a pharmaceutically acceptable carrier, in unit dosage form, each unit dose containing 0.010–0.300 g active ingredient.

* * * * *